US010791517B2

(12) United States Patent
Lu et al.

(10) Patent No.: US 10,791,517 B2
(45) Date of Patent: Sep. 29, 2020

(54) DATA SYNCHRONIZATION METHOD AND APPARATUS, AND TERMINAL DEVICE

(71) Applicant: HUAWEI TECHNOLOGIES CO., LTD., Shenzhen (CN)

(72) Inventors: Chenxi Lu, Shenzhen (CN); Liyao Zhang, Beijing (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 0 days.

(21) Appl. No.: 16/472,896

(22) PCT Filed: Mar. 27, 2017

(86) PCT No.: PCT/CN2017/078278
§ 371 (c)(1),
(2) Date: Jun. 23, 2019

(87) PCT Pub. No.: WO2018/113119
PCT Pub. Date: Jun. 28, 2018

(65) Prior Publication Data
US 2020/0092806 A1 Mar. 19, 2020

(30) Foreign Application Priority Data
Dec. 23, 2016 (CN) .......................... 2016 1 1213342

(51) Int. Cl.
H04W 52/02 (2009.01)
H04W 4/38 (2018.01)
H04L 29/08 (2006.01)

(52) U.S. Cl.
CPC ..... *H04W 52/0216* (2013.01); *H04L 67/1095* (2013.01); *H04W 4/38* (2018.02)

(58) Field of Classification Search
CPC .......... H04W 52/02; H04W 4/38; H04L 29/08
See application file for complete search history.

(56) References Cited

U.S. PATENT DOCUMENTS 9,918,275 B2 * 3/2018 Yu ........................... H04W 4/08
2012/0253220 A1 * 10/2012 Rai ....................... A61B 5/4806
600/544

(Continued)

FOREIGN PATENT DOCUMENTS

AU 2013204229 A1 8/2013
CN 104720753 A 6/2015
(Continued)

*Primary Examiner* — Brenda H Pham
(74) *Attorney, Agent, or Firm* — Kilpatrick Townsend & Stockton LLP

(57) ABSTRACT

A data synchronization method includes: receiving time interval information sent by a second terminal device, where the time interval information includes a synchronization start time and a synchronization end time; obtaining, in stored waking and sleep time information, a time period set that is greater than or equal to the synchronization start time and that is less than or equal to the synchronization end time, where the time period set includes at least one sleep time period; determining, in the time period set, a sleep time period whose sleep duration is greater than a preset threshold; and sending, to the second terminal device, feature data collected in the determined sleep time period.

18 Claims, 4 Drawing Sheets

(56) References Cited

U.S. PATENT DOCUMENTS

2014/0022909 A1* 1/2014 Mahmoud ............. H04L 1/0026
370/241
2015/0281775 A1 10/2015 Ramaswamy et al.
2015/0367097 A1 12/2015 Gavish
2016/0278014 A1* 9/2016 Chen ................. H04W 52/0293

FOREIGN PATENT DOCUMENTS

| CN | 105380600 A | 3/2016 |
| CN | 105610508 A | 5/2016 |
| CN | 105640508 A | 6/2016 |
| CN | 105764409 A | 7/2016 |
| CN | 105877701 A | 8/2016 |
| CN | 105902257 A | 8/2016 |
| CN | 106108843 A | 11/2016 |

* cited by examiner

DATA SYNCHRONIZATION METHOD AND APPARATUS, AND TERMINAL DEVICE

CROSS-REFERENCE TO RELATED APPLICATIONS

This application is a National Stage of International Application No. PCT/CN2017/078278, filed on Mar. 27, 2017, which claims priority to Chinese Patent Application No. 201611213342.7, filed on Dec. 23, 2016. Both of the aforementioned applications are hereby incorporated by reference in their entireties.

TECHNICAL FIELD

This application relates to the field of communications technologies, and in particular, to a data synchronization method and apparatus and a terminal device.

BACKGROUND

Sleep monitoring is an important technology in sleep medicine nowadays. During sleep, a sleep status may be classified into a rapid eye movement stage and a non-rapid eye movement stage based on different sleep depths. A first terminal device may collect feature data such as physiological data or motion data of a user to perform sleep stage analysis, so as to obtain a sleep stage of the user, in other words, determine a sleep status of the user in different time periods. The first terminal device is portable and relatively small in size. However, an operational capability of a processor included in the first terminal device and storage space of a memory included in the first terminal device are often insufficient to support the sleep stage analysis. To avoid the foregoing disadvantage, the first terminal device may synchronize the feature data to a second terminal device such as a smartphone or a computer, so that the second terminal device performs the sleep stage analysis on the feature data to obtain a refined sleep stage. In a process of performing the sleep stage analysis by the second terminal device, if a sleep time period corresponding to the received feature data that is sent by the first terminal device is relatively short, for example, the feature data is collected in a sleep time period less than one hour, the second terminal device cannot obtain the sleep stage of the user.

SUMMARY

Embodiments of the present invention disclose a data synchronization method and apparatus, and a terminal device, so as to avoid a case in which feature data of an effective sleep stage cannot be synchronously supported, and improve data synchronization efficiency.

According to a first aspect, an embodiment of the present invention provides a data synchronization method. A first terminal device may receive time interval information sent by a second terminal device, where the time interval information includes a synchronization start time and a synchronization end time. The first terminal device obtains, in stored waking and sleep time information, a time period set that is greater than or equal to the synchronization start time and that is less than or equal to the synchronization end time, where the time period set includes at least one sleep time period. The first terminal device determines, in the time period set, a sleep time period whose sleep duration is greater than a fourth preset threshold. Then, the first terminal device sends, to the second terminal device, feature data collected in the determined sleep time period.

In the technical solution, the first terminal device determines, in the time period set, the sleep time period whose sleep duration is greater than the fourth preset threshold, and then sends, to the second terminal device, the feature data collected in the determined sleep time period. Compared with a conventional data synchronization method in which the feature data collected in all sleep time periods that are included in the time period set is sent to the second terminal device, this embodiment of the present invention can avoid a case in which feature data of an effective sleep stage cannot be synchronously supported, and improve data synchronization efficiency.

The feature data may include physiological data or motion data of a user. For example, the physiological data may include heart rate information, a snoring degree, a blood pressure value, a respiratory airflow, or the like of the user. The motion data may include a displacement amplitude, frequency, time, or the like of a user limb, and the user limb may include a chest, an abdomen, a hand, a foot, an eye, or the like.

Optionally, the time period set may further include at least one waking and sleep time period. After obtaining, in the stored waking and sleep time information, the time period set that is greater than or equal to the synchronization start time and that is less than or equal to the synchronization end time, the first terminal device may combine a waking and sleep time period that meets a preset rule in the time period set and a sleep time period adjacent to the waking and sleep time period, to obtain an updated sleep time period. Further, that the first terminal device determines, in the time period set, a sleep time period whose sleep duration is greater than a fourth preset threshold may be specifically: determining, in the updated sleep time period, the sleep time period whose sleep duration is greater than the fourth preset threshold.

The waking and sleep time period may indicate a time period in which the user is in a waking state, and the first terminal device may use, as a waking and sleep start time of the waking and sleep time period, a waking time of the user changed from a sleep state to the waking state, and use, as a waking and sleep end time of the waking and sleep time period, a sleep time of the user changed from the waking state to the sleep state.

In the technical solution, when the user changes from the sleep state to the waking state in a sleep process due to an external factor, the waking and sleep time period in the waking state is relatively short, and the user continues to enter the sleep state after the waking and sleep time period is reached (in other words, waking at night). For example, the user hears an alarm during sleeping, and then continues to sleep after turning off the alarm. For another example, the user gets up to go to the toilet due to urgency of urination, and the user continues to sleep after going to the toilet. Based on this, the first terminal device may combine the waking and sleep time period that meets the preset rule and the sleep time period adjacent to the waking and sleep time period, so that the second terminal device performs sleep stage analysis based on the combined sleep time period, and accuracy of the sleep stage analysis may be improved.

Optionally, that the first terminal device combines a waking and sleep time period that meets a preset rule in the time period set and a sleep time period adjacent to the waking and sleep time period, to obtain an updated sleep time period may be specifically: determining, by the first terminal device, that the waking and sleep time period meets the preset rule when waking and sleep duration of the waking and sleep time period in the time period set is less than a first preset threshold; and combining the waking and sleep time period, a previous sleep time period adjacent to the waking and sleep time period, and a next sleep time period adjacent to the waking and sleep time period, to obtain the updated sleep time period.

The sleep time period may indicate a time period in which the user is in the sleep state, and the first terminal device may use, as a sleep start time of the sleep time period, a sleep time of the user changed from the waking state to the sleep state, and use, as a sleep end time of the sleep time period, a waking time of the user changed from the sleep state to the waking state.

In the technical solution, when the waking and sleep duration of the waking and sleep time period in the time period set is less than the first preset threshold, the first terminal device may determine that the user changes from the sleep state to the waking state due to the external factor and continues to enter the sleep state after keeping a short-lived waking state. To prevent the second terminal device from considering the previous sleep time period adjacent to the waking and sleep time period and the next sleep time period adjacent to the waking and sleep time period as two different periods of sleep, the first terminal device may combine the waking and sleep time period, the previous sleep time period adjacent to the waking and sleep time period, and the next sleep time period adjacent to the waking and sleep time period, to obtain the updated sleep time period, so that the second terminal device performs sleep stage analysis based on the updated sleep time period, and accuracy of the sleep stage analysis may be improved.

Optionally, the determining, by the first terminal device, that the waking and sleep time period meets the preset rule when waking and sleep duration of the waking and sleep time period in the time period set is less than a first preset threshold may be specifically: determining, by the first terminal device, that the waking and sleep time period is within a first preset time range; and determining, by the first terminal device, that the waking and sleep time period meets the preset rule when the waking and sleep duration of the waking and sleep time period is less than a second preset threshold corresponding to the first preset time range.

In the technical solution, waking duration of the user in different preset time ranges is different. For example, the waking duration of the user in the daytime is relatively short, and the waking duration of the user at night is relatively long. Then, the first terminal device may establish a correspondence between a preset time range and a preset threshold. For example, the preset threshold corresponding to the first preset time range is the second preset threshold, and the preset threshold corresponding to a second preset time range is a third preset threshold. After the first terminal device determines that the waking and sleep time period is within the first preset time range, the first terminal device may determine that the waking and sleep time period meets the preset rule when the waking and sleep duration of the waking and sleep time period is less than the second preset threshold corresponding to the first preset time range. This embodiment of the present invention may effectively identify whether the previous sleep time period adjacent to the waking and sleep time period and the next sleep time period adjacent to the waking and sleep time period are a same period of sleep, and accuracy of combining sleep time periods may be improved.

Optionally, after receiving the time interval information sent by the second terminal device, the first terminal device may determine the sleep start time in waking and sleep time information based on the synchronization start time, and determine the sleep end time in the waking and sleep time information based on the synchronization end time. Further, that the first terminal device obtains, in stored waking and sleep time information, a time period set that is greater than or equal to the synchronization start time and that is less than or equal to the synchronization end time may be specifically: obtaining, in the waking and sleep time information by the first terminal device, a time period set that is greater than or equal to the sleep start time and that is less than or equal to the sleep end time.

Optionally, that the first terminal device determines the sleep start time in waking and sleep time information based on the synchronization start time may be specifically: using, by the first terminal device, the synchronization start time as the sleep start time, or using a first sleep time in the waking and sleep time information as the sleep start time.

Optionally, that the first terminal device determines the sleep start time in waking and sleep time information based on the synchronization start time may be specifically: using, by the first terminal device, a first sleep time in the waking and sleep time information as the sleep start time when the synchronization start time is earlier than the first sleep time; and using, by the first terminal device, the synchronization start time as the sleep start time when the synchronization start time is later than a first sleep time in the waking and sleep time information.

Optionally, that the first terminal device determines the sleep start time in waking and sleep time information based on the synchronization end time may be specifically: using, by the first terminal device, a last waking time in the waking and sleep time information as the sleep end time.

Optionally, that the first terminal device determines the sleep start time in waking and sleep time information based on the synchronization end time may be specifically: using, by the first terminal device, the synchronization end time as the sleep end time when the synchronization end time is earlier than a last waking time in the waking and sleep time information; and using, by the first terminal device, a last waking time in the waking and sleep time information as the sleep start time when the synchronization end time is later than the last waking time.

According to a second aspect, an embodiment of the present invention provides a computer storage medium, where the computer storage medium stores a program, and when being executed, the program includes all or some steps of the data synchronization method provided in the first aspect of the embodiments of the present invention.

According to a third aspect, an embodiment of the present invention provides a data synchronization apparatus, where the data synchronization apparatus includes a module configured to perform the data synchronization method provided in the first aspect of the embodiments of the present invention.

According to a fourth aspect, an embodiment of the present invention provides a terminal device, including a processor, a memory, and a transceiver, where the memory stores a group of program code, and the processor is configured to invoke the program code stored in the memory, to perform the following operations:

receiving time interval information sent by a second terminal device, where the time interval information includes a synchronization start time and a synchronization end time;

obtaining, in stored waking and sleep time information, a time period set that is greater than or equal to the synchronization start time and that is less than or equal to the synchronization end time, where the time period set includes at least one sleep time period;

determining, in the time period set, a sleep time period whose sleep duration is greater than a fourth preset threshold; and sending, to the second terminal device, feature data collected in the determined sleep time period, where the feature data includes physiological data or motion data of a user.

BRIEF DESCRIPTION OF DRAWINGS

To describe the technical solutions in the embodiments of the present invention or in the background more clearly, the following briefly describes the accompanying drawings required for describing the embodiments of the present invention or the background.

DESCRIPTION OF EMBODIMENTS

The following describes the embodiments of the present invention with reference to the accompanying drawings in the embodiments of the present invention.

Figure 1:
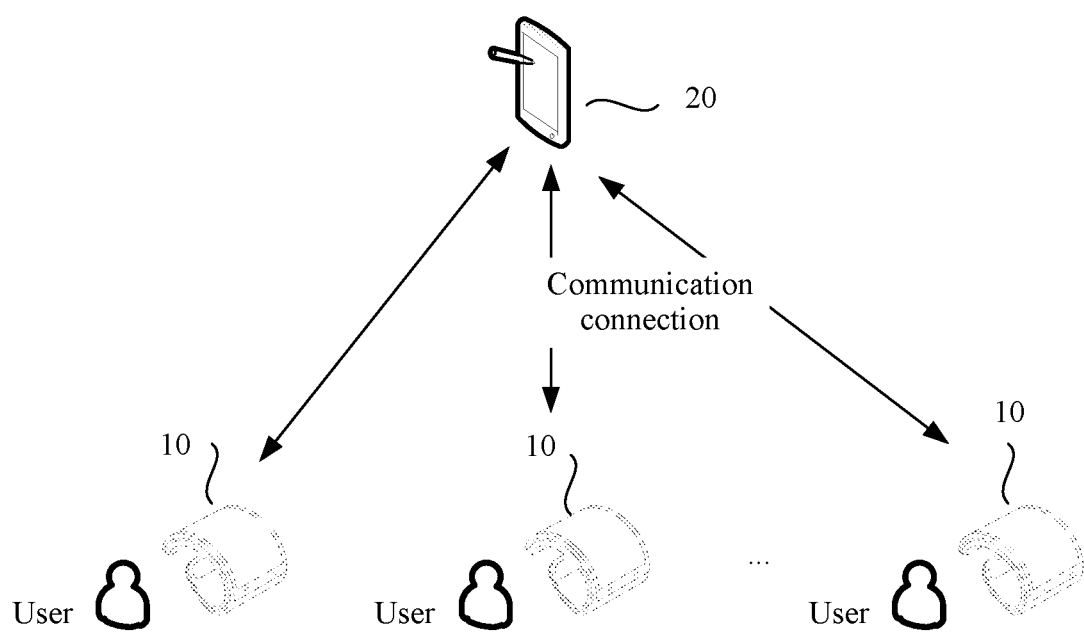
FIG. 1 is a schematic architectural diagram of a data synchronization system according to an embodiment of the present invention.

Referring to FIG. 1, FIG. 1 is a schematic architectural diagram of a data synchronization system according to an embodiment of the present invention. The data synchronization system may include at least one first terminal device 10 and a second terminal device 20. The first terminal device 10 may establish a wired communication connection to the second terminal device 20 by using a twisted pair, a universal serial bus (Universal Serial Bus, USB), or the like. Optionally, the first terminal device 10 may establish a wireless communication connection to the second terminal device 20 through Bluetooth, radio frequency identification (Radio Frequency Identification, RFID), or the like.

The first terminal device 10 may be equipped with a sensor and a photoplethysmogram (Photo Plethysmo Graph, PPG) module. In a specific implementation, the sensor may be configured to collect motion data of a user. For example, when a displacement amplitude, frequency, or a time that is of a user limb and that is collected by the sensor is greater than a preset threshold, it may be determined that the user is in a waking state (namely, a waking state). When a displacement amplitude, frequency, or a time of a user limb is less than or equal to a preset threshold, it may be determined that the user is in a sleep state. When the user is in the sleep state, the first terminal device 10 may control an LED included in the PPG module to emit light. The light penetrates human blood vessels and is reflected. A regular blood vessel contraction caused by a human body pulse changes an intensity of the reflected light, so as to obtain physiological data such as heart rate information.

The first terminal device 10 may be a wearable, surface-mounted or implanted terminal device. If the first terminal device 10 is a wearable terminal device, the first terminal device 10 may be worn on a part of a human body, such as a wrist, an arm, an ankle, or a waist. If the first terminal device 10 is a surface-mounted terminal device, the first terminal device 10 may be attached to a part of the human body, such as the arm, an abdomen, a neck, or a head. If the first terminal device 10 is an implanted terminal device, the first terminal device 10 may be implanted into a part of the human body, such as the wrist, the arm, the head, or a back, in an intrusive manner such as an injection.

The second terminal device 20 may include a smartphone (such as an Android mobile phone and an iOS mobile phone), a tablet computer, a personal computer, or the like.

Figure 2:
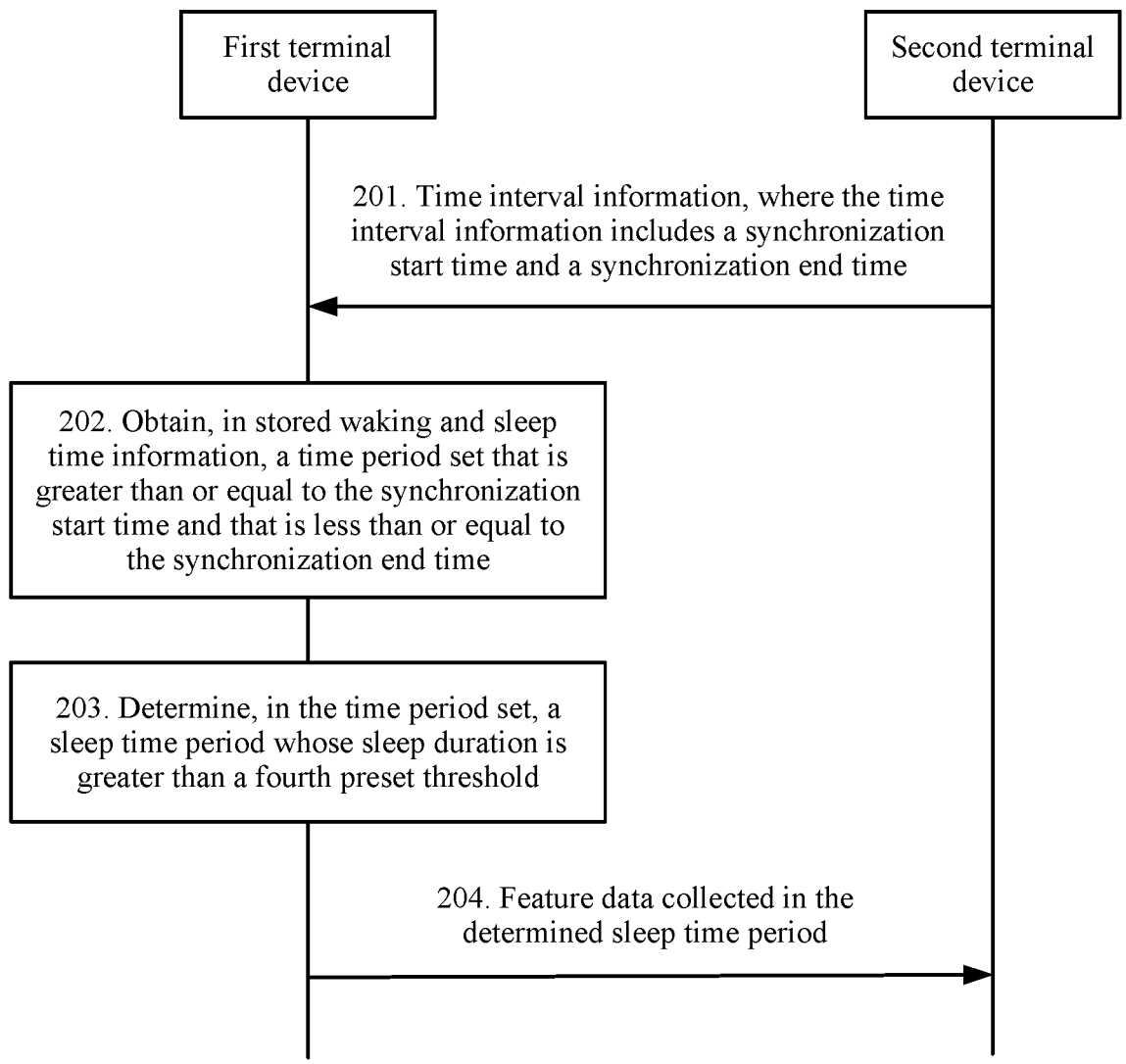
FIG. 2 is a schematic flowchart of a data synchronization method according to an embodiment of the present invention.

Based on a schematic architectural diagram of a data synchronization system shown in FIG. 1, referring to FIG. 2, FIG. 2 shows a data synchronization method according to an embodiment of the present invention. The method includes but is not limited to the following steps.

Step S201. A second terminal device sends time interval information to a first terminal device, where the time interval information includes a synchronization start time and a synchronization end time.

In a specific implementation, when needing to obtain feature data of a user, the second terminal device may send the time interval information to the first terminal device, where the time interval information may include the synchronization start time and the synchronization end time. For example, when needing to obtain the feature data of the user in a time period from 3:00 to 8:00, the second terminal device may generate the time interval information, where the synchronization start time included in the time interval information is 3:00, and the synchronization end time included in the time interval information is 8:00.

Optionally, after receiving the feature data last time sent by the first terminal device, the second terminal device may use an end time point of a sleep time period corresponding to the feature data as the synchronization start time in this data synchronization process, and use a current system time as the synchronization end time in this data synchronization process. Relative to using a synchronization end time submitted in last data synchronization process as the synchronization start time in this data synchronization process, this embodiment of the present invention may prevent the first terminal device from missing the feature data that needs to be synchronized, so as to ensure that the first terminal device feeds back, to the second terminal device, all feature data that meets a requirement in a time interval indicated by the time interval information.

Figure 3:
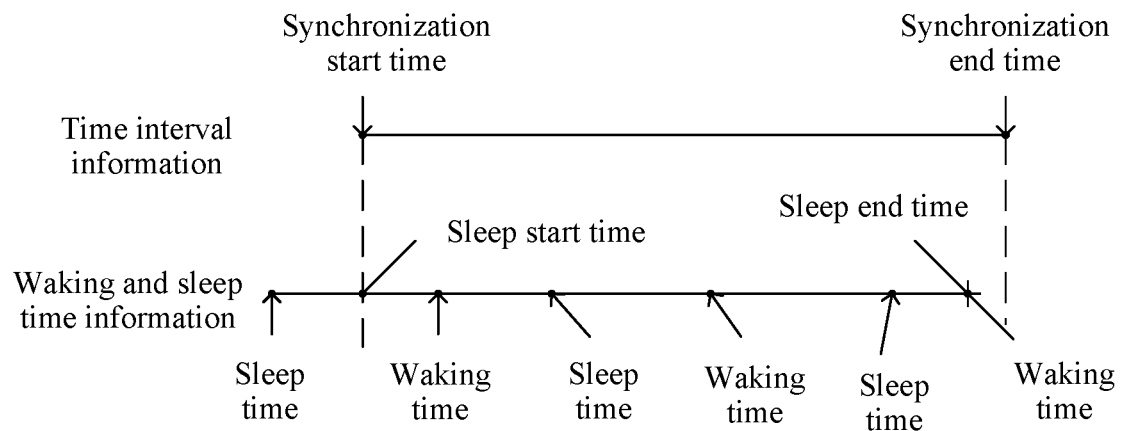
FIG. 3 is a schematic diagram of an interface for waking and sleep time information according to another embodiment of the present invention.

Optionally, after receiving the time interval information sent by the second terminal device, the first terminal device may determine a sleep start time in waking and sleep time information based on the synchronization start time, and determine a sleep end time in the waking and sleep time information based on the synchronization end time. A schematic diagram of waking and sleep time information shown in FIG. 3 is used as an example. The first terminal device may determine, based on the waking and sleep time information, a sleep time changed from a waking state to a sleep state, and a waking time changed from the sleep state to the waking state, then determine the sleep start time in the waking and sleep time information based on the synchronization start time, and determine the sleep end time in the waking and sleep time information based on the synchronization end time.

Optionally, the first terminal device may use the synchronization start time as the sleep start time, or use a first sleep time in the waking and sleep time information as the sleep start time. The schematic diagram of the waking and sleep time information shown in FIG. 3 is used as an example. The first terminal device may compare the synchronization start time with each sleep time, and use, as a start point of the waking and sleep time information, a sleep time that has a minimum difference from the synchronization start time. To be specific, the first sleep time included in the waking and sleep time information is the sleep time that has the minimum difference from the synchronization start time, and then, the first terminal device may use the first sleep time in the waking and sleep time information as the sleep start time. Optionally, the first terminal device may also directly use the synchronization start time as the sleep start time.

Optionally, the first terminal device may use the first sleep time in the waking and sleep time information as the sleep start time when the synchronization start time is earlier than the first sleep time. The first terminal device may use the synchronization start time as the sleep start time when the synchronization start time is later than the first sleep time in the waking and sleep time information. The schematic diagram of the waking and sleep time information shown in FIG. 3 is used as an example. The first terminal device may use, as the start point of the waking and sleep time information, the sleep time that has the minimum difference from the synchronization start time. To be specific, the first sleep time included in the waking and sleep time information is the sleep time that has the minimum difference from the synchronization start time. When the synchronization start time is before the first sleep time, the first terminal device may determine that the synchronization start time is earlier than the first sleep time, and then use the first sleep time as the sleep start time. When the synchronization start time is after the first sleep time, the first terminal device may determine that the synchronization start time is later than the first sleep time, and then use the synchronization start time as the sleep start time.

Optionally, the first terminal device may use a last waking time in the waking and sleep time information as the sleep end time. The schematic diagram of the waking and sleep time information shown in FIG. 3 is used as an example. The first terminal device may compare the synchronization end time with each waking time, and use, as an end point of the waking and sleep time information, a waking time that has a minimum difference from the synchronization end time. To be specific, the last waking time included in the waking and sleep time information is the waking time that has the minimum difference from the synchronization end time, and then, the first terminal device may use the last waking time as the sleep end time.

Optionally, the first terminal device may use the synchronization end time as the sleep end time when the synchronization end time is earlier than the last waking time in the waking and sleep time information. The first terminal device may use the last waking time in the waking and sleep time information as the sleep start time when the synchronization end time is later than the last waking time. The schematic diagram of the waking and sleep time information shown in FIG. 3 is used as an example. The first terminal device may use, as the end point of the waking and sleep time information, the waking time that has the minimum difference from the synchronization end time. When the synchronization end time is before the last waking time, the first terminal device may determine that the synchronization end time is earlier than the last waking time, and then use the synchronization end time as the sleep end time. When the synchronization end time is after the last waking time, the first terminal device may determine that the synchronization end time is later than the last waking time, and then use the last waking time as the sleep end time.

Optionally, after the second terminal device receives the feature data last time sent by the first terminal device, the first terminal device may delete waking and sleep time information obtained last time, so that stored waking and sleep time information is latest waking and sleep time information, and storage space of the first terminal device may be enlarged.

Step S202. The first terminal device obtains, in stored waking and sleep time information, a time period set that is greater than or equal to the synchronization start time and that is less than or equal to the synchronization end time.

In a specific implementation, after receiving the time interval information sent by the second terminal device, the first terminal device may obtain, in the stored waking and sleep time information, the time period set that is greater than or equal to the synchronization start time and that is less than or equal to the synchronization end time. The time period set may include at least one sleep time period. The schematic diagram of the waking and sleep time information shown in FIG. 3 is used as an example. The first terminal device may obtain, in the waking and sleep time information, the time period set that is greater than or equal to the synchronization start time and that is less than or equal to the synchronization end time. A sleep time period included in the time period set may include a time period between the synchronization start time and the first waking time, a time period between a second sleep time and a second waking time, and a time period between a third sleep time and a third waking time.

Optionally, after determining the sleep start time in the waking and sleep time information based on the synchronization start time, and determining the sleep end time in the waking and sleep time information based on the synchronization end time, the first terminal device may obtain, in the waking and sleep time information, a time period set that is greater than or equal to the sleep start time and that is less than or equal to the sleep end time. The schematic diagram of the waking and sleep time information shown in FIG. 3 is used as an example. After using the synchronization start time as the sleep start time, and using the last waking time as the sleep end time, the first terminal device may obtain, in the waking and sleep time information, the time period set that is greater than or equal to the sleep start time and that is less than or equal to the sleep end time. The sleep time period included in the time period set may include the time period between the synchronization start time and the first waking time, the time period between the second sleep time and the second waking time, and the time period between the third sleep time and the third waking time.

Optionally, the time period set may further include at least one waking and sleep time period. The schematic diagram of the waking and sleep time information shown in FIG. 3 is used as an example. A waking and sleep time period included in the time period set may include a time period between the first waking time and the second sleep time, and a time period between the second waking time and the third sleep time.

Further, after obtaining, in the stored waking and sleep time information, the time period set that is greater than or equal to the synchronization start time and that is less than or equal to the synchronization end time, the first terminal device may combine a waking and sleep time period that meets a preset rule in the time period set and a sleep time period adjacent to the waking and sleep time period, to obtain an updated sleep time period. For example, in a sleep process, the user changes from the sleep state to the waking state due to an external factor, a waking and sleep time period in the waking state is relatively short, and the user continues to enter the sleep state after the waking and sleep time period is reached. The first terminal device detects, by using a pre-configured sensor, that the user has two corresponding sleep time periods. However, practically, because the waking and sleep time period of the user in the waking state is relatively short, it may be considered that the foregoing two sleep time periods are a same period of sleep. Based on this, the first terminal device may combine the waking and sleep time period that meets the preset rule in the time period set and the sleep time period adjacent to the waking and sleep time period, to obtain the updated sleep time period.

Optionally, the first terminal device may determine that the waking and sleep time period meets the preset rule when waking and sleep duration of the waking and sleep time period in the time period set is less than a first preset threshold, and then combine the waking and sleep time period, a previous sleep time period adjacent to the waking and sleep time period, and a next sleep time period adjacent to the waking and sleep time period, to obtain the updated sleep time period. The first preset threshold may be preset duration such as 20 minutes or 1 hour.

The schematic diagram of the waking and sleep time information shown in FIG. 3 is used as an example. The first preset threshold is 20 minutes. The first terminal device may determine that the time period between the first waking time and the second sleep time is the waking and sleep time period, the first waking time is 3:00, and the second sleep time is 3:10, the first terminal device may determine that the waking and sleep duration of the waking and sleep time period is a difference between the second sleep time and the first waking time, namely, 10 minutes. The first terminal device may determine that the waking and sleep duration of the waking and sleep time period is less than the first preset threshold, then determine that the waking and sleep time period meets the preset rule, and combine the waking and sleep time period, the previous sleep time period (namely, the time period between the sleep start time and the first waking time) adjacent to the waking and sleep time period, and the next sleep time period (namely, the time period between the second sleep time and the second waking time) adjacent to the waking and sleep time period, to obtain the updated sleep time period. A sleep time of the updated sleep time period is the same as the sleep start time in the waking and sleep time information, and a waking time of the updated sleep time period is the same as the second waking time in the waking and sleep time information.

The schematic diagram of the waking and sleep time information shown in FIG. 3 is used as an example. The first preset threshold is 20 minutes. The first terminal device may determine that the time period between the second waking time and the third sleep time is the waking and sleep time period, the second waking time is 7:00, and the third sleep time is 9:00, the first terminal device may determine that the waking and sleep duration of the waking and sleep time period is a difference between the third sleep time and the second waking time, namely, 2 hours. The first terminal device may determine that the waking and sleep duration of the waking and sleep time period is greater than the first preset threshold, and then determine that the waking and sleep time period does not meet the preset rule. Then, the first terminal device may keep the sleep time period adjacent to the waking and sleep time period unchanged, in other words, does not update the sleep time period adjacent to the waking and sleep time period.

Optionally, the first terminal device may determine that the waking and sleep time period is within a first preset time range, and determine that the waking and sleep time period meets the preset rule when the waking and sleep duration of the waking and sleep time period is less than a second preset threshold corresponding to the first preset time range.

Optionally, the first terminal device may determine that the waking and sleep time period is within a second preset time range, and determine that the waking and sleep time period meets the preset rule when the waking and sleep duration of the waking and sleep time period is less than a third preset threshold corresponding to the second preset time range.

For example, waking duration of the user in different time ranges is different. For example, the waking duration of the user in the daytime is relatively short, and the waking duration at night is relatively long. Based on this, the first terminal device may configure the first preset time range and the second preset threshold corresponding to the first preset time range, and the second preset time range and the third preset threshold corresponding to the second preset time range. For example, the first terminal device may configure the first preset time range as 20:00 to 6:00, the second preset threshold as 1 hour, the second preset time range as 6:00 to 20:00, and the third preset threshold as 20 minutes. The schematic diagram of the waking and sleep time information shown in FIG. 3 is used as an example. The time period between the first waking time and the second sleep time is the waking and sleep time period, the first waking time is 3:00, and the second sleep time is 3:10. Then, the first terminal device may determine that the waking and sleep time period is within the first preset time range and the waking and sleep duration of the waking and sleep time period is the difference between the second sleep time and the first waking time, namely, 10 minutes. Then, the first terminal device may determine that the waking and sleep duration of the waking and sleep time period is less than the second preset threshold, and then determine that the waking and sleep time period meets the preset rule. The schematic diagram of the waking and sleep time information shown in FIG. 3 is used as an example. The time period between the second waking time and the third sleep time is the waking and sleep time period, the second waking time is 7:00, and the third sleep time is 9:00. Then, the first terminal device may determine that the waking and sleep time period is within the second preset time range and the waking and sleep duration of the waking and sleep time period is the difference between the third sleep time and the second waking time, namely, 2 hours. Then, the first terminal device may determine that the waking and sleep duration of the waking and sleep time period is greater than the third preset threshold, and then determine that the waking and sleep time period does not meet the preset rule.

Step S203. The first terminal device determines, in the time period set, a sleep time period whose sleep duration is greater than a fourth preset threshold.

After obtaining, in the stored waking and sleep time information, the time period set that is greater than or equal to the synchronization start time and that is less than or equal to the synchronization end time, the first terminal device may determine, in the time period set, the sleep time period whose sleep duration is greater than the fourth preset threshold. The fourth preset threshold may be specified duration such as 3 hours or 4 hours. The schematic diagram of the waking and sleep time information shown in FIG. 3 is used as an example. The fourth preset threshold is 2 hours. The first terminal device may determine the time period between the sleep start time and the first waking time as the sleep time period, and the sleep duration of the sleep time period is 1 hour. Then, the first terminal device may determine that the sleep duration of the sleep time period is less than the fourth preset threshold. The first terminal device may further determine the time period between the second sleep time and the second waking time as the sleep time period, and the sleep duration of the sleep time period is 3 hours. Then, the first terminal device may determine that the sleep duration of the sleep time period is greater than the fourth preset threshold. The first terminal device may further determine the time period between the third sleep time and the third waking time as the sleep time period, and the sleep duration of the sleep time period is 0.5 hour. Then, the first terminal device may determine that the sleep duration of the sleep time period is less than the fourth preset threshold.

Optionally, after combining the waking and sleep time period that meets the preset rule in the time period set and the sleep time period adjacent to the waking and sleep time period, to obtain the updated sleep time period, the first terminal device may determine that the sleep duration is greater than the sleep time period of the fourth preset threshold in the updated sleep time period. The schematic diagram of the waking and sleep time information shown in FIG. 3 is used as an example. The first terminal device determines the time period between the first waking time and the second sleep time as a waking time period, and the waking time period meets the preset rule. Then, the first terminal device may combine the waking time period, the previous sleep time period adjacent to the waking time period, and the next sleep time period adjacent to the waking time period, to obtain a new sleep time period. In addition, the first terminal device determines the time period between the second waking time and the third sleep time as the waking time period, and the waking time period does not meet the preset rule. Then, the first terminal device may keep the sleep time period adjacent to the waking time period unchanged. Further, the first terminal device may determine that the updated sleep time period includes a time period between the sleep start time and the second waking time and the time period between the third sleep time and the third waking time, the fourth preset threshold is 2 hours, the sleep duration of the time period between the sleep start time and the second waking time is 4.17 hours, and the time period between the third sleep time and the third waking time is 0.5 hour. Then, the first terminal device may determine that the sleep duration of the time period between the sleep start time and the second waking time is greater than the fourth preset threshold, and the sleep duration of the time period between the third sleep time and the third waking time is less than the fourth preset threshold.

Step S204. The first terminal device sends, to the second terminal device, feature data collected in the determined sleep time period.

After determining, in the time period set, that the sleep duration is greater than the sleep time period of the fourth preset threshold, the first terminal device may send, to the second terminal device, the feature data collected in the determined sleep time period. The schematic diagram of the waking and sleep time information shown in FIG. 3 is used as an example. The first terminal device determines that the sleep duration of the time period between the sleep start time and the first waking time is less than the fourth preset threshold. The first terminal device may further determine the time period between the second sleep time and the second waking time as the sleep time period, and the sleep duration of the sleep time period is 3 hours. Then, the first terminal device may determine that the sleep time period is greater than the fourth preset threshold, and send, to the second terminal device, the feature data collected in the sleep time period. The first terminal device may further determine the time period between the third sleep time and the third waking time as the sleep time period, and the sleep duration of the sleep time period is 0.5 hour. Then, the first terminal device may determine that the sleep time period is less than the fourth preset threshold, and refuse to send, to the second terminal device, the feature data collected in the sleep time period.

In the method described in FIG. 2, the time interval information sent by the second terminal device is received, where the time interval information includes the synchronization start time and the synchronization end time; the time period set that is greater than or equal to the synchronization start time and that is less than or equal to the synchronization end time is obtained in the stored waking and sleep time information; the sleep time period whose sleep duration is greater than the fourth preset threshold is determined in the time period set; and the feature data collected in the determined sleep time period is sent to the second terminal device. This can avoid a case in which feature data of an effective sleep stage cannot be synchronously supported, and improve data synchronization efficiency.

The foregoing describes in detail the method in an embodiment of the present invention, and the following provides an apparatus in an embodiment of the present invention.

Figure 4:
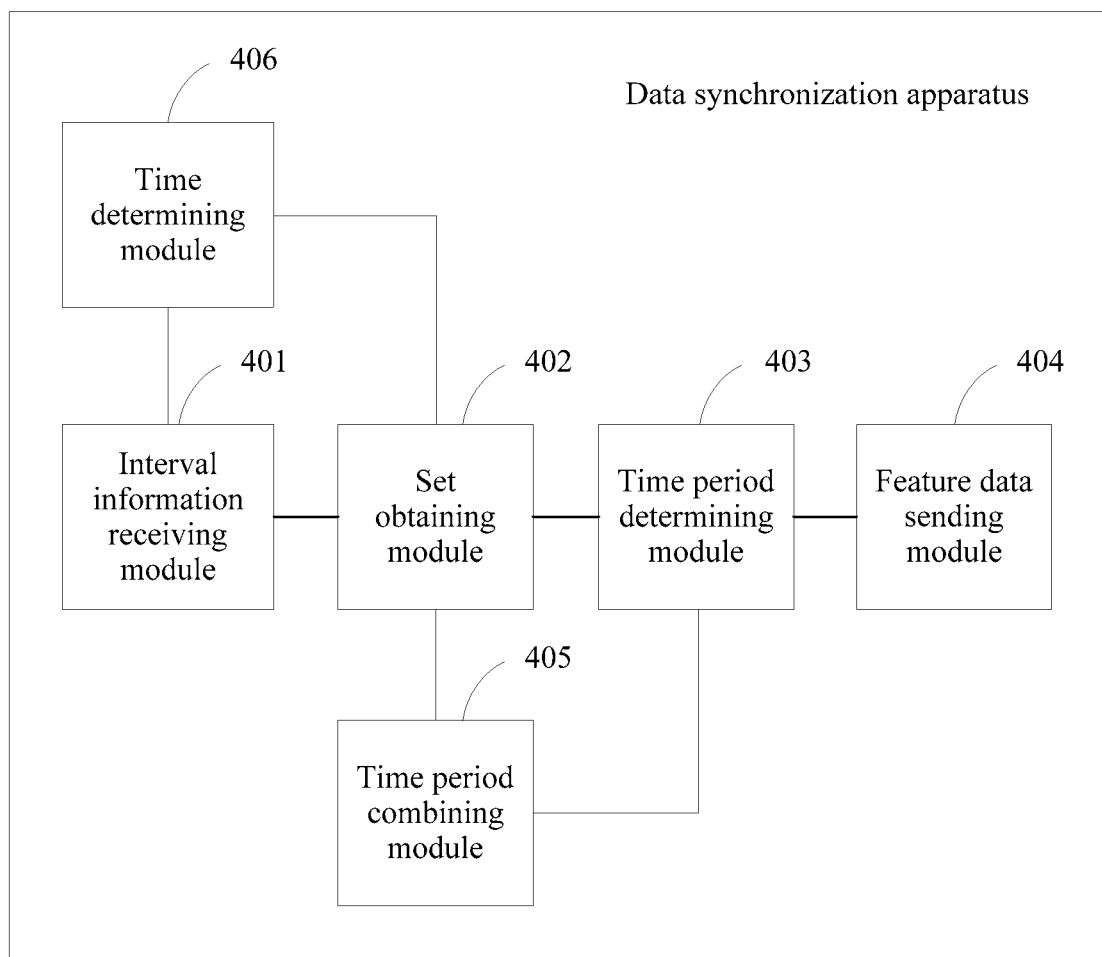
FIG. 4 is a schematic structural diagram of a data synchronization apparatus according to an embodiment of the present invention.

Referring to FIG. 4, FIG. 4 is a schematic structural diagram of a data synchronization apparatus according to an embodiment of the present invention. The data synchronization apparatus may include an interval information receiving module 401, a set obtaining module 402, a time period determining module 403, and a feature data sending module 404. A detailed description of each module is as follows:

The interval information receiving module 401 is configured to receive time interval information sent by a second terminal device, where the time interval information includes a synchronization start time and a synchronization end time.

The set obtaining module 402 is configured to obtain, in stored waking and sleep time information, a time period set that is greater than or equal to the synchronization start time and that is less than or equal to the synchronization end time, where the time period set includes at least one sleep time period.

The time period determining module 403 is configured to determine, in the time period set, a sleep time period whose sleep duration is greater than a fourth preset threshold.

The feature data sending module 404 is configured to send, to the second terminal device, feature data collected in the determined sleep time period, where the feature data includes physiological data or motion data of a user.

Optionally, the time period set further includes at least one waking and sleep time period, and the apparatus may further include:

a time period combining module 405, configured to: after the set obtaining module 402 obtains, in the waking and sleep time information, the time period set that is greater than or equal to the synchronization start time and that is less than or equal to the synchronization end time, combine a waking and sleep time period that meets a preset rule in the time period set and a sleep time period adjacent to the waking and sleep time period, to obtain an updated sleep time period.

Further, the time period determining module 403 is specifically configured to:

determine, in the updated sleep time period, the sleep time period whose sleep duration is greater than the fourth preset threshold.

Optionally, the time period combining module 405 is specifically configured to:

determine that the waking and sleep time period meets the preset rule when waking and sleep duration of the waking and sleep time period in the time period set is less than a first preset threshold; and combine the waking and sleep time period, a previous sleep time period adjacent to the waking and sleep time period, and a next sleep time period adjacent to the waking and sleep time period, to obtain the updated sleep time period.

Optionally, that the time period combining module 405 determines that the waking and sleep time period meets the preset rule when waking and sleep duration of the waking and sleep time period in the time period set is less than a first preset threshold is specifically configured to:

determine that the waking and sleep time period is within a first preset time range; and determine that the waking and sleep time period meets the preset rule when the waking and sleep duration of the waking and sleep time period is less than a second preset threshold corresponding to the first preset time range.

Optionally, the apparatus may further include:

a time determining module 406, configured to: after the interval information receiving module 401 receives the time interval information sent by the second terminal device, determine a sleep start time in the waking and sleep information based on the synchronization start time, and determine a sleep end time in the waking and sleep time information based on the synchronization end time.

Further, the set obtaining module 402 is specifically configured to:

obtain, in the waking and sleep time information, a time period set that is greater than or equal to the sleep start time and that is less than or equal to the sleep end time.

Optionally, that the time determining module 406 determines a sleep start time in the waking and sleep time information based on the synchronization start time may be specifically:

using the synchronization start time as the sleep start time, or using a first sleep time in the waking and sleep time information as the sleep start time.

Optionally, that the time determining module 406 determines a sleep start time in the stored waking and sleep time information based on the synchronization start time is specifically configured to:

use a first sleep time in the waking and sleep time information as the sleep start time when the synchronization start time is earlier than the first sleep time; and use the synchronization start time as the sleep start time when the synchronization start time is later than a first sleep time in the waking and sleep time information.

Optionally, that the time determining module 406 determines a sleep start time in the waking and sleep time information based on the synchronization end time is specifically configured to:

use a last waking time in the waking and sleep time information as the sleep end time.

Optionally, that the time determining module 406 determines a sleep start time in the waking and sleep time information based on the synchronization end time is specifically configured to:

use the synchronization end time as the sleep end time when the synchronization end time is earlier than a last waking time in the waking and sleep time information; and use a last waking time in the waking and sleep time information as the sleep start time when the synchronization end time is later than the last waking time.

In the data synchronization apparatus described in FIG. 4, the interval information receiving module 401 receives the time interval information sent by the second terminal device, where the time interval information includes the synchronization start time and the synchronization end time. The set obtaining module 402 obtains, in the stored waking and sleep time information, the time period set that is greater than or equal to the synchronization start time and that is less than or equal to the synchronization end time. The time period determining module 403 determines, in the time period set, the sleep time period whose sleep duration is greater than the fourth preset threshold. The feature data sending module 404 sends, to the second terminal device, the feature data collected in the determined sleep time period. This can avoid a case in which feature data of an effective sleep stage cannot be synchronously supported, and improve data synchronization efficiency.

Figure 5:
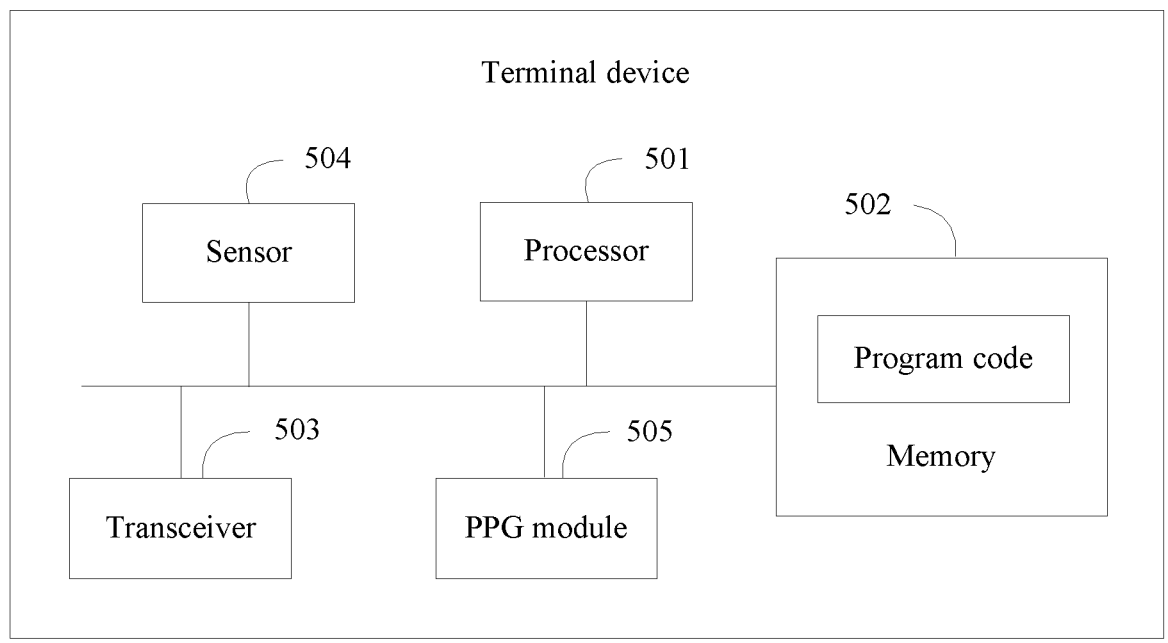
FIG. 5 is a schematic structural diagram of a terminal device according to an embodiment of the present invention.

Referring to FIG. 5, FIG. 5 is a terminal device according to an embodiment of the present invention. The terminal device includes a processor 501, a memory 502, a transceiver 503, a sensor 504, and a PPG module 505. The processor 501, the memory 502, the transceiver 503, the sensor 504, and the PPG module 505 are connected to each other by using a bus.

The memory 502 includes but is not limited to a random access memory (Random Access Memory, RAM), a read-only memory (Read-Only Memory, ROM), an erasable programmable read-only memory (Erasable Programmable Read Only Memory, EPROM), or a compact disc read-only memory (Compact Disc Read-Only Memory, CD-ROM), and the memory 502 is configured to store a related instruction and data, such as waking and sleep time information and feature data. The transceiver 503 is configured to receive and send data, for example, receive time interval information sent by a second terminal device, or send, to the second terminal device, the feature data collected in a determined sleep time period.

The processor 501 may be one or more central processing units (Central Processing Unit, CPU), or one or more micro control units (Microcontroller Unit, MCU). When the processor 501 is one CPU, the CPU may be a single-core CPU, or may be a multi-core CPU.

The sensor 504 may be an accelerometer, a gyroscope, a vibration sensor, or the like, and may obtain a motion status of an associated part of a user.

The PPG module 505 may emit light by using an LED. The light penetrates human blood vessels and is reflected. A regular blood vessel contraction caused by a human body pulse changes an intensity of the reflected light, so as to obtain physiological data such as heart rate information.

The processor 501 in the terminal device is configured to read program code stored in the memory 502, so as to perform the following operations:

receiving, by using the transceiver 503, time interval information sent by a second terminal device, where the time interval information includes a synchronization start time and a synchronization end time;

obtaining, in stored waking and sleep time information, a time period set that is greater than or equal to the synchronization start time and that is less than or equal to the synchronization end time, where the time period set includes at least one sleep time period;

determining, in the time period set, a sleep time period whose sleep duration is greater than a fourth preset threshold; and sending, to the second terminal device by using the transceiver 503, the feature data collected in the determined sleep time period, where the feature data includes the physiological data or motion data of the user.

Optionally, the time period set further includes at least one waking and sleep time period. After obtaining, in the stored waking and sleep time information, the time period set that is greater than or equal to the synchronization start time and that is less than or equal to the synchronization end time, the processor 501 may further perform the following operation:

combining a waking and sleep time period that meets a preset rule in the time period set and a sleep time period adjacent to the waking and sleep time period, to obtain an updated sleep time period.

Further, that the processor 501 determines, in the time period set, a sleep time period whose sleep duration is greater than a fourth preset threshold may be specifically:

determining, in the updated sleep time period, the sleep time period whose sleep duration is greater than the fourth preset threshold.

Optionally, that the processor 501 combines a waking and sleep time period that meets a preset rule in the time period set and a sleep time period adjacent to the waking and sleep time period, to obtain an updated sleep time period may be specifically:

determining that the waking and sleep time period meets the preset rule when waking and sleep duration of the waking and sleep time period in the time period set is less than a first preset threshold; and combining the waking and sleep time period, a previous sleep time period adjacent to the waking and sleep time period, and a next sleep time period adjacent to the waking and sleep time period, to obtain the updated sleep time period.

Optionally, that the processor 501 determines that the waking and sleep time period meets the preset rule when waking and sleep duration of the waking and sleep time period in the time period set is less than a first preset threshold may be specifically:

determining that the waking and sleep time period is within a first preset time range; and determining that the waking and sleep time period meets the preset rule when the waking and sleep duration of the waking and sleep time period is less than a second preset threshold corresponding to the first preset time range.

Optionally, after receiving, by using the transceiver 503, the time interval information sent by the second terminal device, the processor 501 may further perform the following operation:

determining a sleep start time in the waking and sleep time information based on the synchronization start time, and determining a sleep end time in the waking and sleep time information based on the synchronization end time.

Further, that the processor 501 obtains, in stored waking and sleep time information, a time period set that is greater than or equal to the synchronization start time and that is less than or equal to the synchronization end time may be specifically:

obtaining, in the waking and sleep time information, a time period set that is greater than or equal to the sleep start time and that is less than or equal to the sleep end time.

Optionally, that the processor 501 determines a sleep start time in the waking and sleep time information based on the synchronization start time may be specifically:

using the synchronization start time as the sleep start time, or using a first sleep time in the waking and sleep time information as the sleep start time.

Optionally, that the processor 501 determines a sleep start time in the waking and sleep time information based on the synchronization start time may be specifically:

using a first sleep time in the waking and sleep time information as the sleep start time when the synchronization start time is earlier than the first sleep time; and using the synchronization start time as the sleep start time when the synchronization start time is later than a first sleep time in the waking and sleep time information.

Optionally, that the processor 501 determines a sleep start time in the waking and sleep time information based on the synchronization end time may be specifically:

using a last waking time in the waking and sleep time information as the sleep end time.

Optionally, that the processor 501 determines a sleep start time in the waking and sleep time information based on the synchronization end time may be specifically:

using the synchronization end time as the sleep end time when the synchronization end time is earlier than a last waking time in the waking and sleep time information; and using a last waking time in the waking and sleep time information as the sleep start time when the synchronization end time is later than the last waking time.

In the terminal device described in FIG. 5, the processor 501 receives, by using the transceiver 503, the time interval information sent by the second terminal device, where the time interval information includes the synchronization start time and the synchronization end time; obtains, in the stored waking and sleep time information, the time period set that is greater than or equal to the synchronization start time and that is less than or equal to the synchronization end time; determines, in the time period set, the sleep time period whose sleep duration is greater than the fourth preset threshold; and sends, to the second terminal device by using the transceiver 503, the feature data collected in the determined sleep time period. This can avoid a case in which feature data of an effective sleep stage cannot be synchronously supported, and improve data synchronization efficiency.

A person of ordinary skill in the art may understand that all or some of the processes of the methods in the embodiments may be implemented by a computer program instructing relevant hardware. The program may be stored in a computer readable storage medium. When being executed, the program may include the procedures of the foregoing method embodiments. The foregoing storage medium includes any medium that can store program code, such as a ROM, a random access memory RAM, a magnetic disk, or an optical disc.

What is claimed is:

1. A data synchronization method, wherein the method comprises:

receiving time interval information sent by a second terminal device, wherein the time interval information comprises a synchronization start time and a synchronization end time;

obtaining, in stored waking and sleep time information, a time period set that is greater than or equal to the synchronization start time and that is less than or equal to the synchronization end time, wherein the time period set comprises at least one sleep time period;

determining, in the time period set, a sleep time period whose sleep duration is greater than a fourth preset threshold; and sending, to the second terminal device, feature data collected in the determined sleep time period, wherein the feature data comprises physiological data or motion data of a user.

2. The method according to claim 1, wherein the time period set further comprises at least one waking and sleep time period, and after the obtaining, in stored waking and sleep time information, a time period set that is greater than or equal to the synchronization start time and that is less than or equal to the synchronization end time, the method further comprises:

combining a waking and sleep time period that meets a preset rule in the time period set and a sleep time period adjacent to the waking and sleep time period, to obtain an updated sleep time period; and the determining, in the time period set, a sleep time period whose sleep duration is greater than a fourth preset threshold comprises:

determining, in the updated sleep time period, the sleep time period whose sleep duration is greater than the fourth preset threshold.

3. The method according to claim 2, wherein the combining a waking and sleep time period that meets a preset rule in the time period set and a sleep time period adjacent to the waking and sleep time period, to obtain an updated sleep time period comprises:

determining that the waking and sleep time period meets the preset rule when waking and sleep duration of the waking and sleep time period in the time period set is less than a first preset threshold; and combining the waking and sleep time period, a previous sleep time period adjacent to the waking and sleep time period, and a next sleep time period adjacent to the waking and sleep time period, to obtain the updated sleep time period.

4. The method according to claim 3, wherein the determining that the waking and sleep time period meets the preset rule when waking and sleep duration of the waking and sleep time period in the time period set is less than a first preset threshold comprises:

determining that the waking and sleep time period is within a first preset time range; and determining that the waking and sleep time period meets the preset rule when the waking and sleep duration of the waking and sleep time period is less than a second preset threshold corresponding to the first preset time range.

5. The method according to claim 1, after the receiving time interval information sent by a second terminal device, further comprising:

determining a sleep start time in the waking and sleep time information based on the synchronization start time, and determining a sleep end time in the waking and sleep time information based on the synchronization end time; and the obtaining, in stored waking and sleep time information, a time period set that is greater than or equal to the synchronization start time and that is less than or equal to the synchronization end time comprises:

obtaining, in the waking and sleep time information, a time period set that is greater than or equal to the sleep start time and that is less than or equal to the sleep end time.

6. The method according to claim 5, wherein the determining a sleep start time in the waking and sleep time information based on the synchronization start time comprises:

using the synchronization start time as the sleep start time; or using a first sleep time in the waking and sleep time information as the sleep start time.

7. The method according to claim 5, wherein the determining a sleep start time in the waking and sleep time information based on the synchronization start time comprises:

using a first sleep time in the waking and sleep time information as the sleep start time when the synchronization start time is earlier than the first sleep time; and using the synchronization start time as the sleep start time when the synchronization start time is later than a first sleep time in the waking and sleep time information.

8. The method according to claim 5, wherein the determining a sleep end time in the waking and sleep time information based on the synchronization end time comprises:

using a last waking time in the waking and sleep time information as the sleep end time.

9. The method according to claim 5, wherein the determining a sleep end time in the waking and sleep time information based on the synchronization end time comprises:

using the synchronization end time as the sleep end time when the synchronization end time is earlier than a last waking time in the waking and sleep time information; and using a last waking time in the waking and sleep time information as the sleep start time when the synchronization end time is later than the last waking time.

10. A terminal device, comprising:

a non-transitory memory comprising instructions; and at least one processor coupled to the non-transitory memory, the instructions being executed by the at least one processor to cause the terminal device to be configured to:

receive time interval information sent by a second terminal device, wherein the time interval information comprises a synchronization start time and a synchronization end time;

obtain, in stored waking and sleep time information, a time period set that is greater than or equal to the synchronization start time and that is less than or equal to the synchronization end time, wherein the time period set comprises at least one sleep time period;

determine, in the time period set, a sleep time period whose sleep duration is greater than a fourth preset threshold; and send feature data collected in the determined sleep time period to the second terminal device, wherein the feature data comprises physiological data or motion data of a user.

11. The terminal device according to claim 10, wherein the time period set further comprises at least one waking and sleep time period, the instructions further cause the terminal device to:

combine a waking and sleep time period that meets a preset rule in the time period set and a sleep time period adjacent to the waking and sleep time period, to obtain an updated sleep time period; and determine, in the updated sleep time period, the sleep time period whose sleep duration is greater than the fourth preset threshold.

12. The terminal device according to claim 11, the instructions further cause the terminal device to:

determine that the waking and sleep time period meets the preset rule when waking and sleep duration of the waking and sleep time period in the time period set is less than a first preset threshold; and combine the waking and sleep time period, a previous sleep time period adjacent to the waking and sleep time period, and a next sleep time period adjacent to the waking and sleep time period, to obtain the updated sleep time period.

13. The terminal device according to claim 12, the instructions further cause the terminal device to:

determine that the waking and sleep time period is within a first preset time range; and determine that the waking and sleep time period meets the preset rule when the waking and sleep duration of the waking and sleep time period is less than a second preset threshold corresponding to the first preset time range.

14. The terminal device according to claim 10, the instructions further cause the terminal device to:

determine a sleep start time in the waking and sleep time information based on the synchronization start time, and determining a sleep end time in the waking and sleep time information based on the synchronization end time; and obtain, in the waking and sleep time information, a time period set that is greater than or equal to the sleep start time and that is less than or equal to the sleep end time.

15. The terminal device according to claim 14, the instructions further cause the terminal device to:

use the synchronization start time as the sleep start time; or use a first sleep time in the waking and sleep time information as the sleep start time.

16. The terminal device according to claim 14, the instructions further cause the terminal device to:

use a first sleep time in the waking and sleep time information as the sleep start time when the synchronization start time is earlier than the first sleep time; and use the synchronization start time as the sleep start time when the synchronization start time is later than a first sleep time in the waking and sleep time information.

17. The terminal device according to claim 14, the instructions further cause the terminal device to:

use a last waking time in the waking and sleep time information as the sleep end time.

18. The terminal device according to claim 14, the instructions further cause the terminal device to:

use the synchronization end time as the sleep end time when the synchronization end time is earlier than a last waking time in the waking and sleep time information; and use a last waking time in the waking and sleep time information as the sleep start time when the synchronization end time is later than the last waking time.

* * * * *